United States Patent [19]

Labeda et al.

[11] Patent Number: 4,628,046
[45] Date of Patent: Dec. 9, 1986

[54] ANTIBIOTIC LL-C23201δ

[75] Inventors: David P. Labeda, Monsey; Joseph J. Goodman, Spring Valley; John H. E. J. Martin, deceased, late of New York, all of N.Y., by Mary B. Martin, executrix

[73] Assignee: American Cyanamid Company, Stamford, Conn.

[21] Appl. No.: 506,170

[22] Filed: Jun. 20, 1983

[51] Int. Cl.[4] .............................................. A61K 31/71
[52] U.S. Cl. .................................... 514/33; 536/16.1; 536/16.8; 536/18.1; 514/23
[58] Field of Search ..................... 536/16.1, 16.8, 18.1; 424/180; 514/23

[56] References Cited

U.S. PATENT DOCUMENTS 4,269,971 5/1981 Yamagishi et al. ................ 536/16.8
4,278,663 7/1981 Liu et al. ............................. 536/16.8

Primary Examiner—Johnnie R. Brown
Assistant Examiner—Elli Peselev
Attorney, Agent, or Firm—M.-E. M. Timbers

[57] ABSTRACT

This disclosure describes a new antibacterial agent designated LL-C23201δ, produced in a microbiological fermentation under controlled conditions using a new strain of Streptomyces olivaceo-griseus, sp. nov. and mutants thereof. This new antibacterial agent is active against a variety of microorganisms and thus is useful in inhibiting the growth of such bacteria wherever they may be found.

7 Claims, 4 Drawing Figures

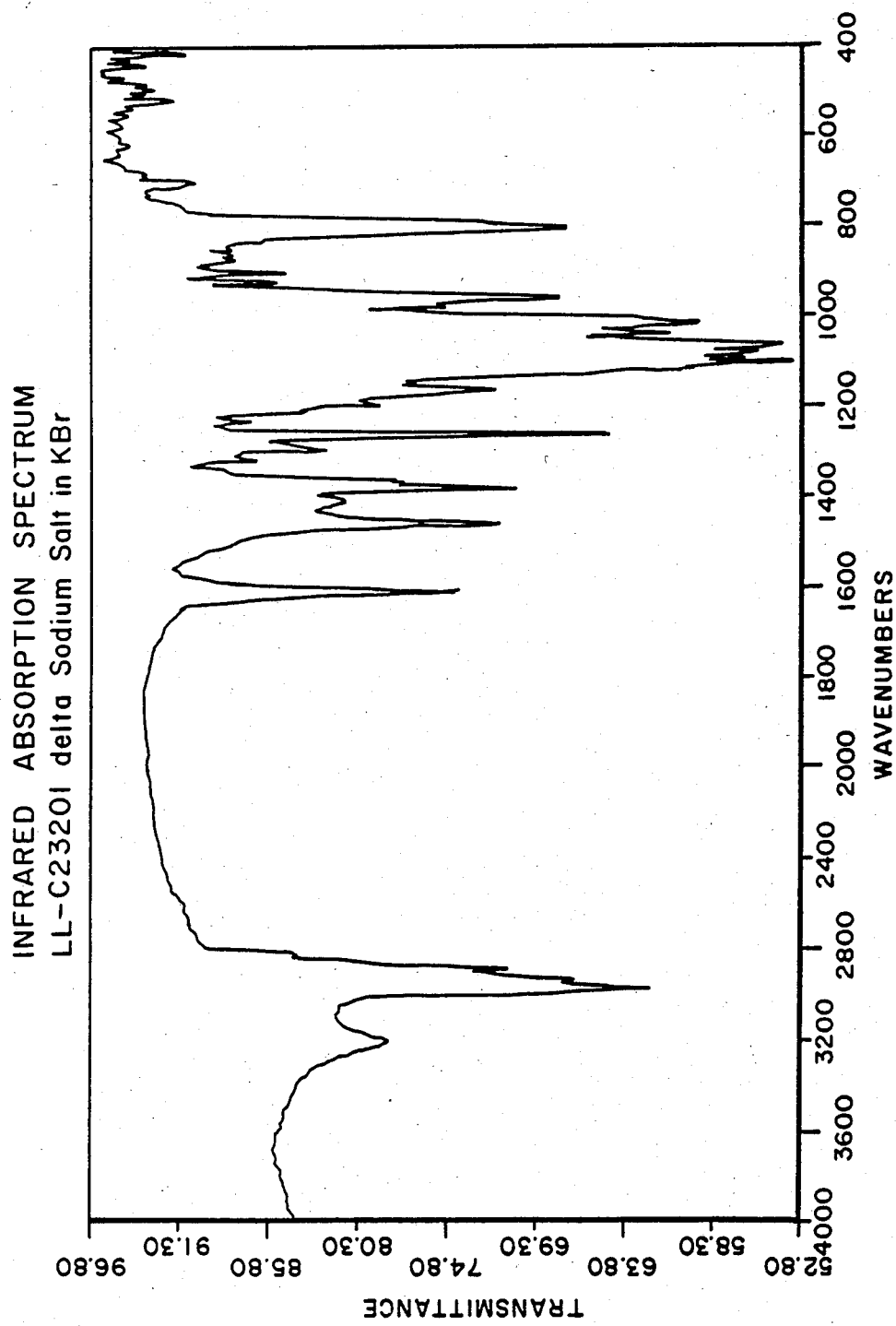

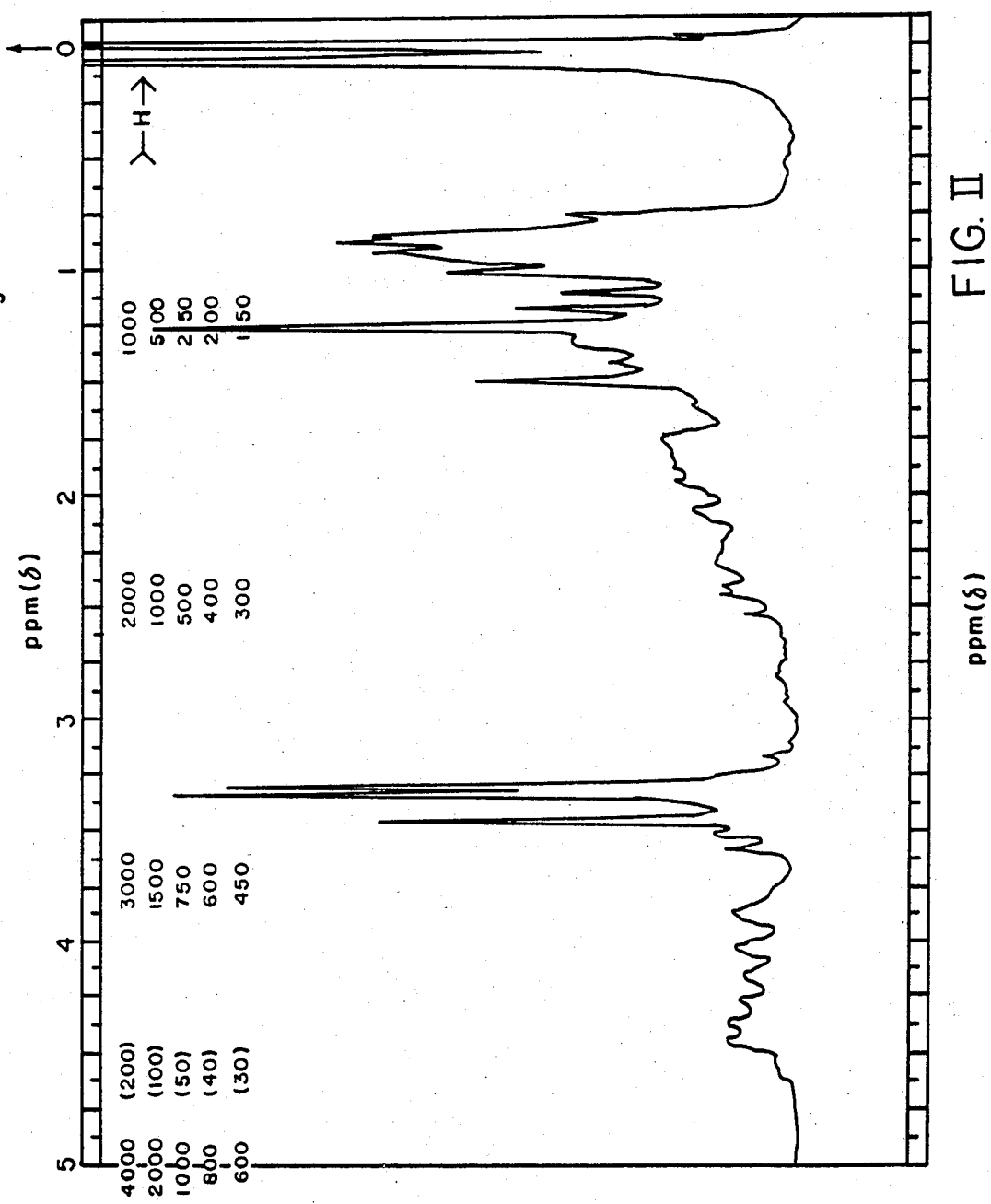
FIG. II

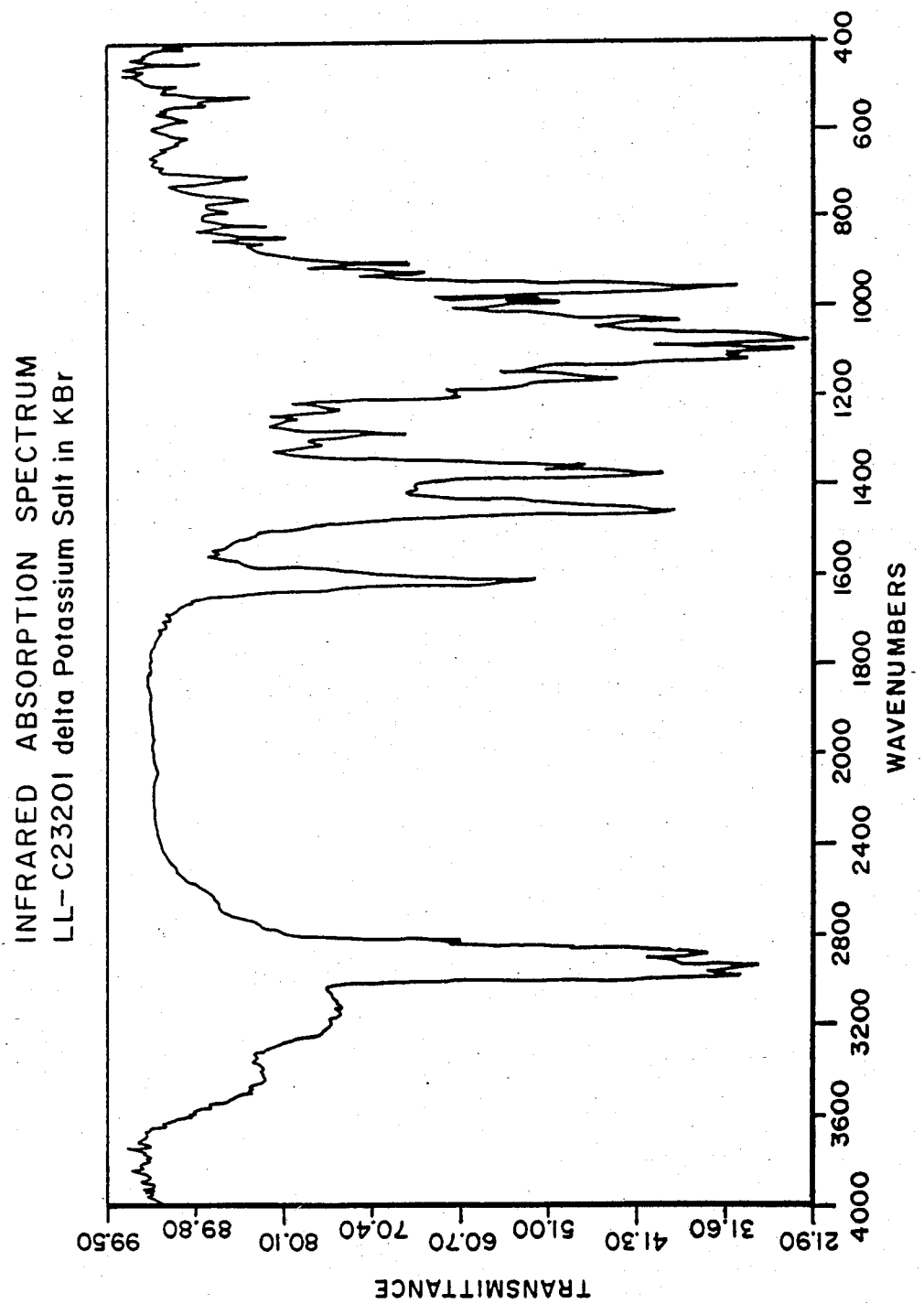

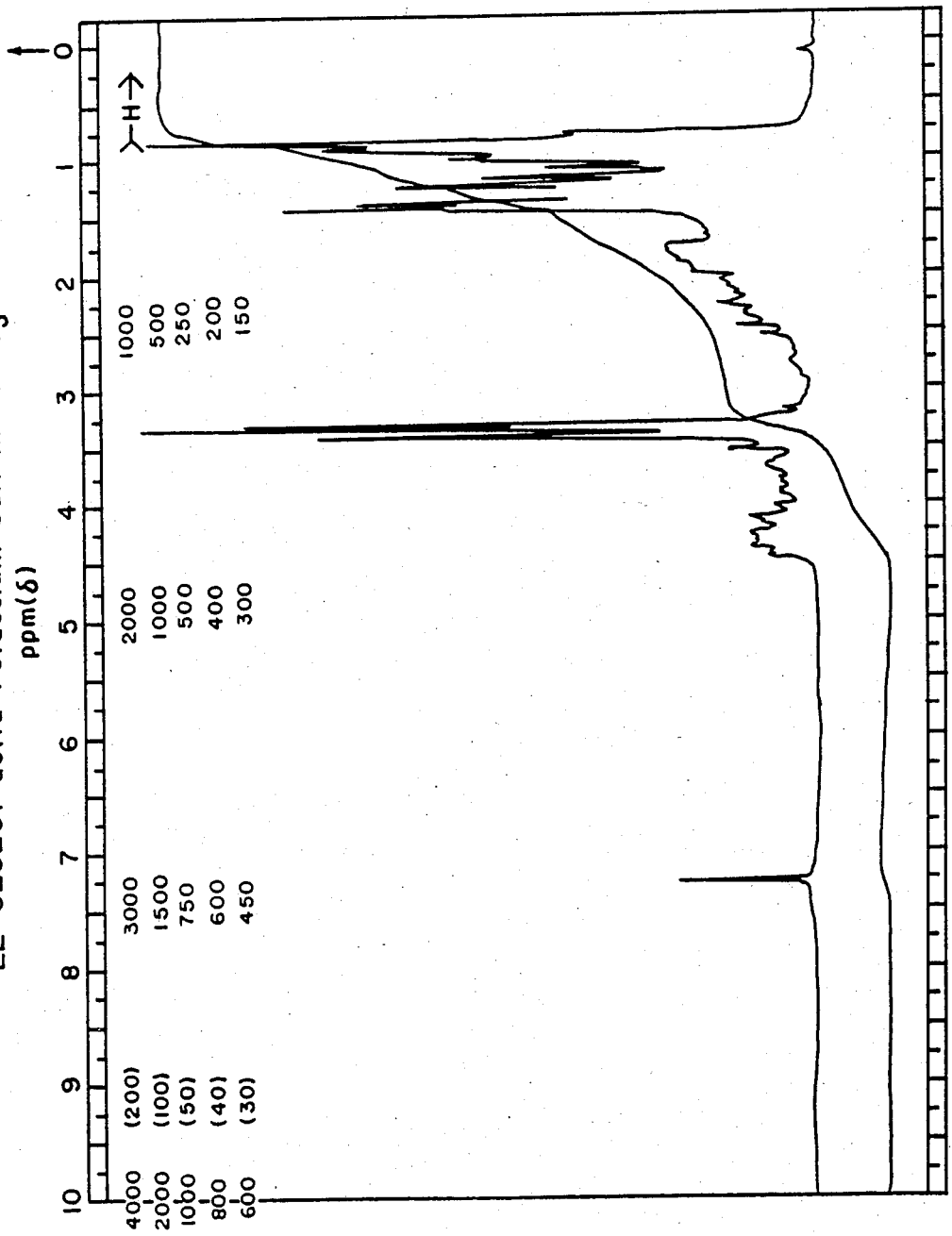

ANTIBIOTIC LL-C23201δ

BRIEF SUMMARY OF THE INVENTION

This invention relates to a new antibacterial agent designated LL-C23201δ, to its production by fermentation, to methods for its recovery and concentration from crude solutions and to processes for its purification. The present invention includes within its scope the antibacterial agent in dilute form, as a crude concentrate and in pure crystalline form. The effects of this new antibacterial agent on specific microorganisms, together with its chemical and physical properties, differentiate it from previously described antibacterial agents.

The molecular structure of LL-C23024δ was determined by X-ray crystallography of the rubidium salt, and it has the following formula:

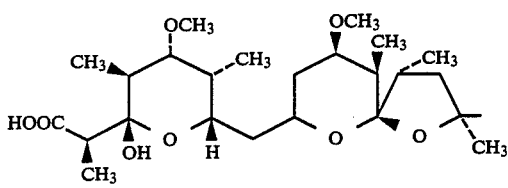

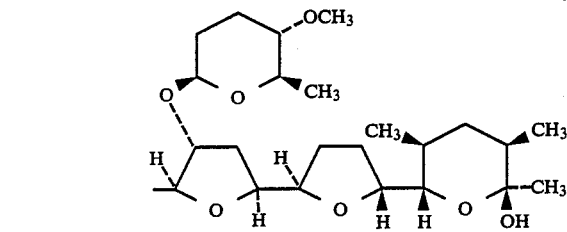

LL-C23201δ is a new polyether antibiotic useful as an antibacterial and anticoccidial agent. Field desorption mass spectroscopy indicates that the sodium salt has a molecular weight of 907 and the potassium salt a molecular weight of 923. Further characterization of LL-C23201δ is detailed in the Examples and is shown in the accompanying FIGS. I-IV:

FIG. I: IR spectrum of LL-C23201δ sodium salt in KBr.

FIG. II: PMR spectrum 79.5 MHz in CDCl$_3$ of LL-C23201δ sodium salt.

FIG. III: IR spectrum of LL-C23201δ potassium salt in KBr.

FIG. IV: PMR spectrum 79.5 MHz in CDCl$_3$ of LL-C23201δ potassium salt.

The $^{13}$CNMR spectrum of the sodium salt of LL-C23201δ was obtained using a Varian FT80 instrument at 20 MHz in CDCl$_3$. The chemical shifts for both the sodium salt of the antibiotic 6016 [J. Antibiotics, 32, 244-246 (1979)] [Otake, N., et al., J. Chem. Soc. Chem. Comm., 875-876 (1978)] which is a polyther antibiotic and the sodium salt of LL-C23201δ are given in Table I.

TABLE I

| $^{13}$CNMR Spectra of Sodium Salt, LL-C23201δ, and Antibiotic 6016 | | | |
|---|---|---|---|
| LL-C23201δ C$_{47}$H$_{80}$O$_{15}$ | Antibiotic 6016 C$_{46}$H$_{78}$O$_{16}$ | LL-C23201δ | Antibiotic 6016 |
| 5.0 | 5.0 | 39.7 | 39.4 |
| 11.5 | — | 46.0 | — |
| 11.7 | 11.7 | 55.9 | 55.8 |

TABLE I-continued

| $^{13}$CNMR Spectra of Sodium Salt, LL-C23201δ, and Antibiotic 6016 | | | |
|---|---|---|---|
| LL-C23201δ C$_{47}$H$_{80}$O$_{15}$ | Antibiotic 6016 C$_{46}$H$_{78}$O$_{16}$ | LL-C23201δ | Antibiotic 6016 |
| 12.6 | 12.5 | 56.8 | 56.7 |
| 13.1 | 13.0 | 58.8 | 58.8 |
| 16.9 | 16.8 | 61.1 | 60.9 |
| 17.3 | 17.3 | 64.3 | 64.8 |
| 18.3 | 18.2 | — | 72.1 |
| 24.3 | 24.3 | 74.3 | 73.9 |
| 26.4 | 26.5 | 74.6 | 74.4 |
| 27.0 | 26.9 | 74.9 | 74.6 |
| 28.1 | 28.0 | 78.7 | 78.6 |
| 29.1 | 29.1 | 78.9 | 79.0 |
| 30.6 | 30.5 | 79.8 | 79.6 |
| 30.8 | 30.6 | 80.2 | 79.9 |
| 31.5 | 31.2 | 80.5 | 80.7 |
| 32.8 | 32.7 | 82.5 | 82.3 |
| 34.3 | 33.4 | 82.8 | 82.6 |
| 35.3 | 34.0 | 90.0 | 89.9 |
| 36.9 | 36.5 | 96.8 | 96.6 |
| 36.9 | 36.7 | 99.2 | 98.2 |
| 37.5 | 36.9 | 100.1 | 99.2 |
| 39.1 | 38.9 | 108.1 | 107.9 |
| 39.4 | 39.3 | 180.5 | 178.4 |
| | | 47 × C | 46 × C |

The above spectra show that LL-C23201δ has 47 carbons and the structure shown herein.

The antibiotic 6016 has 46 carbons and its structure is:

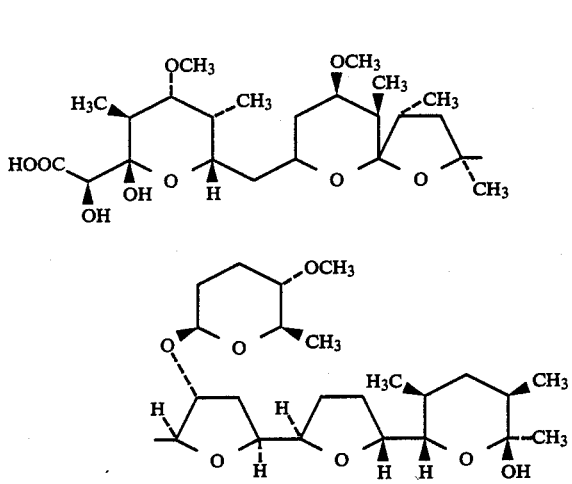

Antibiotic LL-C23201δ is an organic carboxylic acid and thus is capable of forming salts with non-toxic pharmaceutically acceptable cations. Thus, salts formed by admixture of the antibiotic free acid with stoichiometric amounts of cations, suitably in a neutral solvent, may be formed with cations such as sodium, potassium, calcium, magnesium and ammonium, as well as organic amine cations such as tri(lower alkyl)amine (e.g., triethylamine, triethanolamine), procaine and the like. The cationic salts of antibiotic LL-C23024δ are, in general, crystalline solids, relatively insoluble in water but are soluble in most common organic solvents such as methanol, ethyl acetate, acetone, chloroform, heptane, ether and benzene.

DETAILED DESCRIPTION OF THE INVENTION

The new antibacterial agent LL-C23201δ is formed during the cultivation under controlled conditions of a new species of Streptomyces named *Streptomyces olivaceo-griseus* sp. nov.

This new antibiotic strain was isolated as an aerial contaminant at the Medical Research Division, American Cyanamid Company, Pearl River, N.Y. and is maintained in the culture collection of the aforesaid Medical Research Division as culture member LL-C23201. A viable culture of this new microorganism has been deposited with the Culture Collection Laboratory, North Central Region, Northern Regional Center, U.S. Department of Agriculture, Peoria, Ill. and has been added to its permanent collection. It is freely available to the public from this depository under its accession number NRRL 15357.

TAXONOMIC CHARACTERIZATION OF CULTURE LL-C23201

The culture LL-C23201 was taxonomically characterized and identified as a new species of the gray-spored Streptomyces to be known as *Streptomyces olivaceo-griseus*, sp. nov.

Observations were made of the cultural, physiological, and morphological features of the culture in accordance with the methods detailed by Shirling, E. B. and Gottlieb, D., Internat. J. Syst. Bacteriol. 16, 313–340 (1966). Media used in this study were selected from those recommended by Pridham, T. G., et. al., Antibiotics Annual, pp. 947–953 (1956/57) and Gordon R. E., et. al., Internat. J. Syst. Bacteriol. 24, 54–63 (1974) for the taxonomic study of actinomycetes and soil bacteria, respectively. Chemical composition of the cell walls of the culture was determined using the method of Lechevalier, et. al., Adv. Appl. Microbiol. 14, 47–72 (1971). Details are recorded in Tables I–V, and a general description of the culture is given below. Underscored descriptive colors are taken from Kelly, K. L. and Judd, D. B., Nat. Bur. Stand., Spec. Publ. 440 (1976) and the accompanying Inter-Society Color Council, National Bureau of Standards, Centroid Color Charts.

Isolate LL-C23201 was compared to an appropriate reference strain, *Streptomyces ravidus* NRRL 11300, the culture which produce ravidomycin. A comparison of 14-day growth of each of these cultures on Hickey-Tresner agar is shown below:

| CULTURE | SPORE MASS COLOR | SOLUBLE PIGMENTS | REVERSE COLOR |
| --- | --- | --- | --- |
| S. ravidus NRRL 11300 | Light Gray | Red | Grayish Reddish Brown |
| S. olivaceo-griseus LL-C23201 | Light Gray | None | Blackish Green |

The gross colonial morphology of LL-C23201 does not resemble *S. ravidus*, and significant differences were also observed in physiology. *S. ravidus* reduces nitrates and utilizes arabinose but does not utilize mannitol or sucrose. A search of the current streptomycete literature failed to reveal any described species which resembled LL-C23201; therefore, a new species is designated to be known as *Streptomyces olivaceo-griseus*, sp. nov.

MICROMOPHOLOGY

Spores are formed in coiled chains (Spira) on aerial sporophores. The spores are ovoid (1.5–1.8 microns by 2.0–2.5 microns), and the surface of the mature spores is smooth when observed by scanning electron microscopy.

CELL WALL COMPOSITION

Whole cell hydrolysates of this culture contain the L,L-isomer of diaminopimelic acid, placing it in the Type I cell wall group of Lechevalier, et al. (vide supra). This is typical of all Streptomyces species.

AMOUNT OF GROWTH

Good growth is observed on most media; moderate growth is observed on glycerol-asparagine agar; poor growth is observed on oatmeal agar; no growth is observed on tomato paste-oatmeal agar.

AERIAL MYCELIUM AND SPORE COLOR

Aerial mycelium is white on most media but becomes tinged with pink or inorganic salts-starch agar; spore masses are 264. light gray in color.

SOLUBLE PIGMENTS

Absent on many media; brownish shades where produced.

REVERSE COLOR

Greenish black to olive black shades on all media.

PHYSIOLOGICAL REACTIONS

Nitrates not reduced to nitrites in 14 days; no liquifaction of gelatin in 14 days; no black pigment (melanin) produced on either peptone-yeast extract-iron agar or tyrosine agar; strong peptonization of litmus milk in 14 days. Carbohydrate utilization as per the method of Pridham, T. G., and Gottlieb, D. J., Bacteriol., 56, 107–144 (1948), good utilization of glucose; moderate utilization of fructose and inositol; poor utilization of galactose, mannitol, rhamnose, or salicin. Several organic acids were tested as sole carbon sources: citrate, malate, and succinate were strongly utilized; lactate was weakly utilized; and benzoate, mucate, and oxalate were not utilized. Adenine, hypoxanthine, and tyrosine were hydrolysed in 14 days, while guanine and xanthine were not.

TABLE I

Cultural Characteristics of *Streptomyces olivaceo-griseus* LL-C23201
Incubation 14 days    Temperature: 28° C.

| Medium | Amount of Growth | Aerial Mycelium and/or Spores | Soluble Pigment | Reverse Color |
| --- | --- | --- | --- | --- |
| Glycerol-Asparagine Agar | Moderate | Relatively flat, waxy growth with no aerial mycelia; growth 77. moderate yellowish brown | Brownish | Greenish black |
| Hickey-Tresner Agar | Good | Raised waxy colonies with plicate centers; vegetative growth 152, blackish green; very little aerial mycelia or spore production; spores 264. light gray | none | Blackish green |

TABLE I-continued

Cultural Characteristics of *Streptomyces olivaceo-griseus* LL-C23201
Incubation 14 days    Temperature: 28 ° C.

| Medium | Amount of Growth | Aerial Mycelium and/or Spores | Soluble Pigment | Reverse Color |
|---|---|---|---|---|
| Inorganic Salt-Starch Agar | Moderate to Good | Slightly raised waxy colonies; 110 grayish olive to 114, olive black, becoming powdery in sporulating areas; aerial mycelia white to 28. light grayish pink in areas; spores 264. light gray | None | — |
| Nz-amine Glucose Starch Agar | Good | Raised ridged growth; vegetative mycelia 157. greenish black; heavy production of aerial mycelia and spores; spores 264. light gray | Brownish | Greenish black |
| Oatmeal Agar | Poor | Flat, dull growth with no aerial mycelia; vegetative mycelia 90. grayish yellow to 112. light olive gray | None | — |
| Yeast Extract Malt Extract Agar | Good | Raised, ridged colonies with heavy sporulation; vegetative mycelia 114. olive black; spore mass 264. light gray | Brown | Olive Black |

TABLE II

Micromorphology of *Streptomyces olivaceo-griseus* LL-23201

| Medium | Aerial Mycelium and/or Sporiferous Structures | Spore Shape | Spore Size | Spore Surface |
|---|---|---|---|---|
| Inorganic Salts-Starch Agar | Spore chains arise as coiled chains from aerial (Spira) | Ovoid | 0.6–0.7 micron X 0.6–0.8 micron | Smooth |

TABLE III

Physiological Reaction of *Streptomyces olivaceo-griseus* LL-C23201

| Medium | Incubation Period (days) | Amount of Growth | Physiological Reaction |
|---|---|---|---|
| Peptone-Iron Agar | 7 | Good | No Blackening |
|  | 14 | Good | No blackening |
| Tyrosine Agar (ISP-7) | 7 | Good | No blackening |
|  | 14 | Good | Greenish Black pigment |
| Litmus Milk | 7 | Good | Slight proteolysis |
|  | 14 | Good | Strong proteolysis |
| Nutrient Gelatin | 7 | Slight | No proteolysis |
|  | 14 | Slight | No Proteolysis |
| Nitrate Broth | 7 | Good | No reduction |
|  | 14 | Good | No reduction |
| Adenine Agar | 7 | Good | Strong hydrolysis |
|  | 14 | Good | Strong hydrolysis |
| Guanine Agar | 7 | Good | No hydrolysis |
|  | 14 | Good | No hydrolysis |
| Hypoxanthine Agar | 7 | Good | No hydrolysis |
|  | 14 |  | Strong hydrolysis |
| Tyrosine Agar | 7 | Good | No hydrolysis |
|  | 14 | Good | Weak hydrolysis |
| Xanthine Agar | 7 | Good | No hydrolysis |
|  | 14 | Good | No hydrolysis |

TABLE IV

Carbon Source Utilization of *Streptomyces olivaceo-griseus* LL-C23201
Incubation: 14 Days    Temperature: 28° C.

| Carbon Source | Utilization* |
|---|---|
| l-Arabinose | 0 |
| Fructose | 2 |
| d-Galactose | 1 |
| d-Glucose | 3 |
| l-Inositol | 2 |
| d-Mannitol | 1 |
| d-Raffinose | 0 |
| l-Rhamnose | 0 |
| Salicin | 0 |
| Sucrose | 1 |
| Xylose | 1 |
| Negative control | 0 |

*3 = Good utilization
2 = Fair Utilization
1 = Poor Utilization
0 = No Utilization

TABLE V

Utilization of organic acids
*Streptomyces olivaceo-griseus*
LL-C23201 on Gordon's modification
Koser's basal agar
(Koser's citrate agar)
Incubation: 14 Days    Temperature: 28° C.

| Carbon Source | Utilization |
|---|---|
| Benzoate | — |
| Citrate | + |
| Lactate | ± |
| Malate | + |
| Mucic Acid | — |
| Oxalate | — |
| Succinate | + |

It is to be understood that for the production of this antibacterial agent, the present invention is not limited to this particular organism or to organisms fully answering the above growth and microscopic characteristics, which are given for illustrative purposes only. In fact, it is desired and intended to include the use of mutants produced from this organism by various means such as exposure to X-radiation, ultraviolet radiation, nitrogen mustard, actinophages, and the like.

This antibactrial agent is active in vitro against gram-positive bacteria (Table VI) and against gram-positive and gram-negative anaerobes (Table VII).

TABLE VI

Antibacterial Activity of LL-C23201δ
Agar Dilution Method, Meuller-Hinton Agar

| Gram-Positive Organism | Minimal Inhibitory Concentration (mcg/ml) |
|---|---|
| *Staphylococcus aureus* Smith | 0.5 |
| *Staphylococcus aureus* SSC80-11 | 1 |
| *Staphylococcus aureus* SSC80-32 | 1 |
| *Staphylococcus aureus* SSC80-38 | 1 |
| *Staphylococcus aureus* LL-14 | 0.5 |
| *Staphylococcus aureus* LL-45 | 0.5 |
| *Staphylococcus aureus* LL-27 | 2 |
| *Staphylococcus aureus* ATCC25923 | 0.5 |
| *Streptococcus pyogenes* C203 | $\leq 0.12$ |
| *Streptococcus* β-hemdytic Keller T623 | $\leq 0.12$ |
| *Streptococcus pneumoniae* 78-1 | 0.25 |
| *Enterococcus* SSC80-62 | 0.5 |
| *Enterococcus* SSC80-63 | 0.5 |

TABLE VII

Activity of LL-C23201δ Against Anaerobic
Bacteria Agar-Dilution, Wilkins-Chalgren Agar,
Incubated in a Gas-Pac at 37° C. for 48 hours

| Organism | No. of Strains Tested | Minimal Inhibitory Concentration mcg/ml Range |
|---|---|---|
| *Bacteroides fragilis* | 13 | 8–256 |
| *Bacteroides thetaiotaomicron* | 5 | 16–256 |
| *Bacteroides vulgatus* | 2 | 8 |
| *Bacteroides distasonis* | 1 | $\leq 0.12$ |
| *Clostridium perfringens* | 2 | $\leq 0.12$ |
| *Clostridium innocuum* | 1 | $\leq 0.12$ |
| *Clostridium bifermentans* | 1 | $\leq 0.12$ |
| *Clostridium difficile* | 1 | $\leq 0.12$ |
| *Peptococcus anaerobius* | 1 | $\leq 0.12$ |
| *Peptococcus magnus* | 1 | $\leq 0.12$ |

In addition, LL-C23201δ is active in vitro and in vivo as an anticoccidial agent. In tissue culture it is active against *Eimeria tenella* at 0.001 to 0.1 ppm. It is active in chicks against *Eimeria tenella* and *Eimeria acervulina* in the range of 10–125 ppm.

GENERAL PROCEDURE FOR THE PRODUCTION OF LL-C23201δ

Cultivation of *Streptomyces olivaceo-griseus* NRRL 15357 may be carried out in a wide variety of liquid culture media. Media which are useful for the production of this novel antibacterial agent include an assimilable source of carbon such as starch, sugar, molasses, glycerol, etc., an assimilable source of nitrogen such as protein, protein hydrolysate, polypeptides, amino acids, corn steep liquor, etc., and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is provided by forcing sterile air through or onto the surface of the fermenting medium. Further agitation in tanks is provided by a mechanical impeller. An antifoaming agent such as lard oil may be added as needed.

INOCULUM PREPARATION

Shaker flask inoculum of *Streptomyces olivaceo-griseus* NRRL 15357 is prepared by inoculating 100 ml of sterile liquid medium in 500 ml flasks with scrapings or washings of spores from an agar slant of the culture. The following is an example of a suitable medium:

| Beef extract | 0.3% |
|---|---|
| Bacto tryptone | 0.5% |
| Glucose | 1.0% |
| Yeast extract | 0.5% |
| Bacto agar | 0.15% |
| Water qs | 100% |

The flasks are incubated at a temperature of 25°–35° C., preferably 32° C. and agitated vigorously on a rotary shaker for 24–28 hours.

Portions of the above flask inoculum are then used to inoculate multi-liter portions of the same sterile medium in bottles which are aerated with sterile air while growth is continued for 24–48 hours. This bottle inoculum is then used to inoculate a seed tank fermentor containing 30–300 liters of the same sterile medium which is grown for 18–24 hours at 32° C. with aeration and then used to inoculate tank fermentors.

TANK FERMENTATION

For the production of LL-C23201δ in tank fermentors the following sterilized medium may be used:

| Glucose | 1.5% |
|---|---|
| Glycerol | 1.5% |
| Soy flour | 1.5% |
| Calcium carbonate | 0.1% |
| Sodium chloride | 0.3% |
| Water qs | 100% | pH adjusted to 7.0 with 6N sodium hydroxide

Each tank is inoculated with 3–10% of inoculum prepared as described above. Aeration is supplied at the rate of 0.5 to 2.0 liter of sterile air per liter of broth per minute and the fermenting medium is agitated by an impeller driven at 100–400 rpm. The temperature is maintained at 25°–35° C., preferably at 32° C. The fermentation is usually continued for 100–150 hours, at which time the mash is harvested.

EXAMPLE 1

Inoculum Preparation

A typical medium used to grown the primary inoculum was prepared according to the following formula:

| Beef extract | 0.3% |
|---|---|
| Bacto tryptone | 0.5% |
| Glucose | 1.0% |
| Yeast extract | 0.5% |
| Bacto agar | 0.15% |
| Water qs | 100% |

Scraped spores from an agar slant of *Streptomyces olivaceo-griseus* NRRL 15357 were used to inoculate two 500 ml flasks each containing 100 ml of the above sterilized medium. The flasks were placed on a rotary shaker and agitated vigorously for 24 hours at 32° C. The resulting flask inoculum (200 ml) was used to inoculate 12 liters of the same sterile medium in a 15 liter bottle. This bottle inoculum was aerated with sterile air while growth was continued for 48 hours at 28° C. This bottle inoculum (12 liters) was then used to inoculate 300 liters of the same sterile medium in a seed fermentation tank. This seed inoculum was grown, with aeration, for 18 hours at 32° C.

EXAMPLE 2

Fermentation

A fermentation medium was prepared according to the following formulation:

| | |
|---|---|
| Glucose | 1.5% |
| Glycerol | 1.5% |
| Soy flour | 1.5% |
| Calcium carbonate | 0.1% |
| Sodium chloride | 0.3% |
| Water qs to | 100% |

The pH was adjusted to 7.0 with 6N sodium hydroxide prior to sterilization. A 300 liter portion of the seed inoculum (Example 1) was used to inoculate 2600 liters of the above medium in a large tank fermentor. Sterile aeration was supplied to the mash which was agitated by an impeller driven at 100 rpm. The fermentation was carried out at 32° C. for 116 hours at which time the mash was harvested.

EXAMPLE 3

Preliminary Isolation of LL-C23201δ

A total of 3000 liters of harvest mash (Example 2) was adjusted to pH 4.0, using 6N hydrochloric acid and was then stirred with ½ of its volume of methylene chloride. The mixture was filtered through diatomaceous earth, then the organic solvent layer was drawn off, washed with aqueous sodium bicarbonate solution and concentrated in vacuo to 6.5 liters of a viscous oily residue.

A glass column with a diameter of 8.5 cm was packed dry to a height of 97 cm with Woelm silica gel TSC. An 1100 ml portion of the above oily residue was diluted with 2 liters of methylene chloride and allowed to seep into the column. This column was developed first with 11 liters of methylene chloride:ethyl acetate (3:1) and then with 4 liters of ethyl acetate. Fractions of 60 ml each were collected and checked for antibacterial activity by the bioautography of impregnated paper discs on large agar plates at pH 6.0 seeded with *Bacillus subtilis* Stansley R-78. Fractions 124–136 were combined and concentrated in vacuo, giving 1765 mg of active residue.

A glass column with a diameter of 4.5 cm was packed dry to a height of 84 cm with Woelm silica gel TSC. The above active residue (1765 mg) was dissolved in 50 ml of methylene chloride and allowed to seep into the column which was then developed with methylene chloride:ethyl acetate (1:1) collecting fractions of 45 ml each. The fractions were again checked by bioautography and the active fractions were combined and desolventized in vacuo, giving LL-C23201δ as a viscous residue.

EXAMPLE 4

Preparation of the Crystalline Sodium Salt of LL-C23201δ

The purified residue, prepared in Example 3, was dissolved in 200 ml of hexane:ether (1:1) and then placed over dilute hydrochloride acid (7 ml of 0.1N hydrochloric acid and 150 ml of water). The two phases were thoroughly mixed, allowed to settle and the acidic aqueous portion discarded. The organic layer was washed twice with 200 ml volumes of water. The washed organic layer was transferred over 150 ml of fresh water and dilute sodium hydroxide was added dropwise until the pH stabilized between 10.5 and 11.0 after shaking and settling. The organic layer was again washed twice with 200 ml volumes of water and was then dried over sodium sulfate, concentrated in vacuo to about 30 ml and then allowed to stand at 4° C. for 2 hours. The crystals that formed were collected, washed with cold hexane and air dried, giving 1223 mg of the sodium salt of LL-C23201δ, having the following characteristics:

Elemental analysis: C, 57.29; H, 8.59; ash, 5.34.
Molecular weight (F.D. mass spectroscopy): 907.
$[\alpha]_D^{22} = -28°$ (0.49% in methanol).
MP=164°–168° C.
Infra red spectrum in KBr as shown in FIG. I;
UV spectra shows only weak end absorption;
Proton magnetic resonance spectrum 79.5 MHz in CDCl$_3$ using a Varian FT80 as shown in FIG. II.

EXAMPLE 5

Preparation of the Crystalline Potassium Salt of LL-C23201δ

A 540 mg portion of purified LL-C23201δ, prepared as described in Example 3 was treated as described in Example 4, substituting potassium hydroxide for sodium hydroxide. The yield was 332 mg of the white crystalline potassium salt of LL-C23201δ, having the following characteristics:

Elemental analysis: C, 60.83; H, 8.60; ash, 4.20.
Melting point 167° C.
Molecular weight (F.D. mass spectroscopy)=923.
$[\alpha]_D^{22} = -28°$ (0.49% in methanol).
Infrared spectrum in KBr as shown in FIG. IV.
Proton magnetic resonance spectrum 79.5 MHz in CDCl$_3$ using a Varian FT80 as shown in FIG. IV.

EXAMPLE 6

High Performance Liquid Chromatography of LL-C23201δ

LL-C23201δ using the following conditions for analytical high performance chromatography:
Instrument: Waters ALC/GPC 244
Column: Ultrasphere ODS, pH 5.0/methanol (10/90)
Detector: Refractive index, 4×setting
LL-C23201δ was homogeneous and had a retention time of 22.3 minutes.

We claim:
1. The compound LL-C23201δ of the formula:

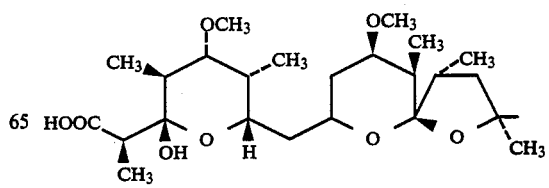

-continued

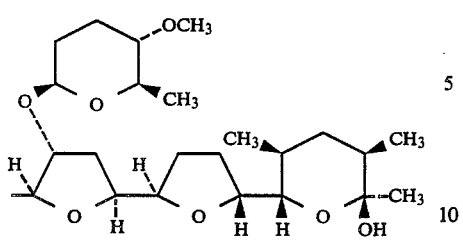

and the pharmaceutically-acceptable salts thereof.

2. The sodium salt of antibiotic compound LL-C23201δ, as recited in claim 1 wherein the substantially pure form has:
 (a) Elemental analysis: C, 57.29; H, 8.59;
 (b) Molecular weight by field absorption mass spectroscopy of 907;
 (c) Optical rotation $[\alpha]_D^{22} = -28°$ (0.49% methanol);
 (d) Melting point 164°–168° C.;
 (e) Characteristic infrared absorption spectrum as shown in FIG. I of the attached drawings; and
 (f) Characteristic proton magnetic resonance spectrum as shown in FIG. II of the attached drawings.

3. The potassium salt of the antibiotic compound LL-C23201δ as recited in claim 1, wherein the substantially pure form has:
 (a) Elemental analysis: C, 60.83; H, 8.60;
 (b) Molecular weight by field absorption mass spectroscopy of 923;
 (c) Optical rotation $[\alpha]_D^{22} = -28°$ (0.49% in methanol);
 (d) Melting point 167° C.;
 (e) Characteristic infrared absorption spectrum as shown in FIG. III of the attached drawings; and
 (f) Characteristic proton magnetic resonance spectrum as shown in FIG. IV of the attached drawings.

4. A method of treating bacterial infections in warm-blooded animals comprising administering to said animals an antibacterially-effective amount of antibiotic LL-C23201δ of the formula

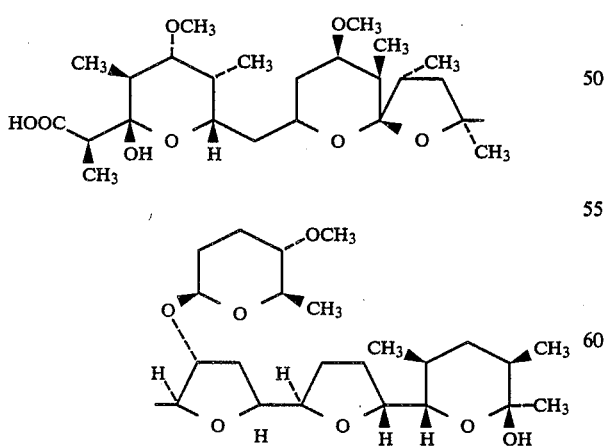

5. An antibacterial pharmaceutical composition of matter comprising an antibacterial effective amount of antibiotic LL-C23201δ of the formula

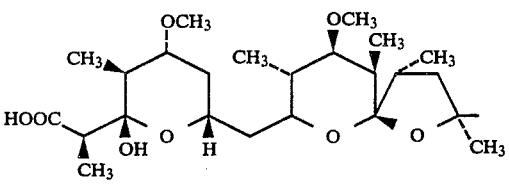

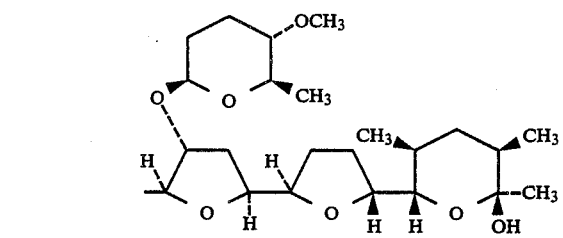

or the pharmaceutically-acceptable salts thereof and a pharmaceutical carrier.

6. A composition for the control of coccidiosis infections in poultry comprising a coccidiostatic amount of the compound LL-C23201δ of the formula

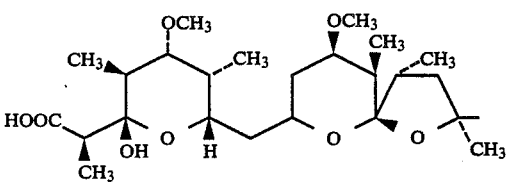

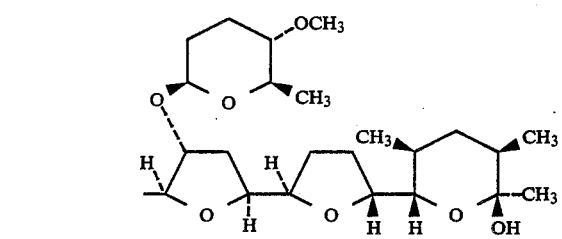

or the pharmaceutically-acceptable salts thereof and an edible carrier therefor.

7. A method for the control of coccidiosis infections in poultry comprising orally administering to said poultry a coccidially-effective amount of the compound LL-C23201δ of the formula

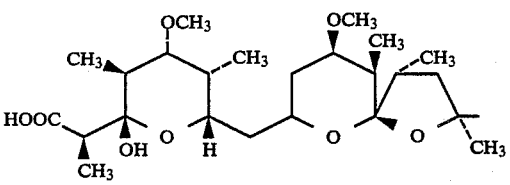

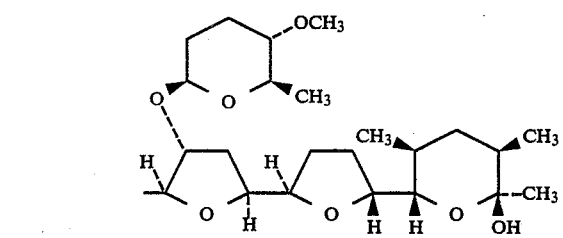

or the pharmaceutically-acceptable salts thereof.

* * * * *